United States Patent [19]

Cort

[11] 4,235,881

[45] Nov. 25, 1980

[54] METHOD FOR PRODUCING HIGH POTENCY FACTOR VIII

[76] Inventor: Joseph H. Cort, 300 E. 54 St., New York, N.Y. 10022

[21] Appl. No.: 966,014

[22] Filed: Dec. 4, 1978

[51] Int. Cl.³ .................... A61K 35/14; A61K 37/00
[52] U.S. Cl. .................................. 424/101; 424/177; 260/112.5 R
[58] Field of Search ................ 260/112.5 R; 424/177, 424/101

[56] References Cited

U.S. PATENT DOCUMENTS

| | | | |
|---|---|---|---|
| 3,454,549 | 7/1969 | Boissonnas | 260/112.5 R |
| 3,497,491 | 2/1970 | Zaoral et al. | 260/112.5 R |
| 3,980,631 | 9/1976 | Prochazka et al. | 260/112.5 R |
| 4,157,431 | 6/1979 | Fields et al. | 424/177 |

OTHER PUBLICATIONS

Colin R., et al., Chemical Abstract, vol. 66, 84660p (1967).
Hershgold, E., et al., Chemical Abstracts, vol. 74 94474k (1971).
Cash, J., et al., Clinical Science and Molecular Medicine, 54, pp. 403–409 (1978).
Mannucci et al., The Lancet, 8017c, pp. 869–872 (1977).
Cort et al., *Molecular Endocrinology*, pp. 337–349, Holland Biomedical Press (1977).
Aberg, M., et al., Chemical Abstract, vol. 84, 41626m, 1976.

*Primary Examiner*—Delbert R. Phillips
*Assistant Examiner*—Blondel Hazel
*Attorney, Agent, or Firm*—Kenyon & Kenyon

[57] ABSTRACT

Factor VIII preparations of enhanced potency are obtained from human blood donors by recovering blood from donors who have been treated with vasopressin analogs, such as 1-deamino-6-carba-8-D-arginine vasopressin, in an amount sufficient to increase the circulating blood level of Factor VIII in the donor.

6 Claims, No Drawings

METHOD FOR PRODUCING HIGH POTENCY FACTOR VIII

The present invention is concerned with a more concentrated, and hence more active form of Factor VIII, antihemophilic factor, and with a method for producing it.

BACKGROUND

It is known that the clotting of human blood is a complicated process, involving a series of reactions mediated by 13 different factors. It also is well known that a cause of hemophilia is the inability of the afflicted individual to synthesize one of these factors, known variously as antihemophilic factor, AHF, AHG or Factor VIII, in amounts sufficient to support adequate clotting. About 40 percent of hemophiliacs have no ability to synthesize Factor VIII, while the others have diminished ability. Dried preparations of Factor VIII concentrate are sold commercially for administration to hemophiliacs for treatment of bleeding or in advance of surgery. The Factor VIII concentrate is obtained from plasma obtained from human donors, through the use of known techniques. At the time of use, the dried concentrate is dissolved in sterile water, and the resulting solution is administered intravenously.

The Factor VIII preparation is not pure Factor VIII. Rather, it is a Factor VIII-enriched fraction obtained from plasma and contains other components. It is highly desirable that the Factor VIII concentrate be as pure as possible, but further improvements in purity through modification of the procedure for isolating Factor VIII from plasma are not practically feasible due to the difficulty of separating plasma components.

DESCRIPTION OF THE INVENTION

In accordance with this invention, Factor VIII having increased purity and potency is obtained from the plasma of donors having elevated levels of Factor VIII obtained by administration to such donor a polypeptide analog of vasopressin represented by the general formula:

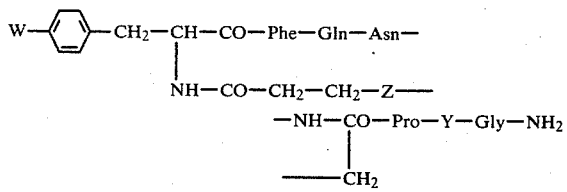

wherein W is hydrogen, hydroxy or amino; Y is a residue of an alpha-amino acid having a basic aliphatic side chain in the D-configuration containing from 2 to 5 carbon atoms and having on the terminal carbon a basic group such as the amino or guanidino group, such as arginine, lysine and ornithine; and Z is a disulfide (—S—S—) or monocarba (—S—CH$_2$—) radical; with the proviso that when W is hydroxy, and Y is D-arginine, then Z is monocarba. By the term "residue" of an amino acid is meant the divalent radical formed by removal of the hydrogen atom from the alpha-amino group and the removal of the hydroxyl group from the carboxyl group of the amino acid. According to accepted conventions, Phe represents the residue of phenylalanine, Gln represents the residue of glutamine, Asn represents the residue of asparagine, Pro represents the residue of proline and Gly represents the residue of glycine.

Polypeptides within the scope of the general formula (I) are disclosed in U.S. Pat. No. 3,980,631. These, as well as still other polypeptides within the scope of the formula, may be synthesized from individual amino acids or amino acid precursors by procedures described in U.S. Pat. No. 3,980,631. The currently preferred polypeptide within the above-defined class of vasopressin analogs is 1-deamino-6-carba-8-D-arginine vasopressin, also known as 6-monocarba desmopressin or dCDAVP. The preparation of this polypeptide is described in Example 2 of U.S. Pat. No. 3,980,631.

These polypeptides are known to be pharmaceutically useful as antidiuretics. More recently, however, it has been reported by Mannucci et al in "1-Deamino-8-D-Arginine Vasopressin: A New Pharmacological Approach to the Management of Haemophilia and Von Willebrand's Disease," The Lancet, (i) 869 (1977), that when a related vasopressin analog, dDAVP, is administered to those hemophiliacs having diminished ability to synthesize Factor VIII, the ability to synthesize Factor VIII can be increased to normal levels.

It has now been discovered in accordance with this invention that the administration of polypeptide vasopressin analogs defined above to non-hemophiliacs causes them to synthesize amounts of Factor VIII substantially in excess (e.g., of the order of from about 3 to about 10 times) of the normal amount. That is, when the polypeptide is administered to a normal human, the concentration of Factor VIII in the plasma increases above normal levels by from about 3 to about 10 times. On the other hand, the increased levels of Factor VIII do not cause an undesirable increase in the rate of clotting in normal humans. Apparently this is due, at least in part, to the fact that the levels of one or more of the other factors involved in clotting are such that the overall clotting reaction cannot proceed at a rate greater than normal, despite the presence of elevated levels of Factor VIII. In addition, it appears that administration of the polypeptide to humans also increases the level of plasminogen activator, which is known to inhibit or reduce clotting. The increased levels of plasminogen activator may serve to protect against increased clotting. Regardless of theory, however, it has been shown that the polypeptide can be administered to normal humans at levels which cause substantial increases in the circulating level of Factor VIII without significant change in clotting and without significant side-effect other than antidiuresis. This latter effect poses no problem, however, since it is accompanied by inhibition of thirst and there is no danger of voluntary overhydration.

The amount of polypeptide which is effective to increase the circulating level of Factor VIII ordinarily is an amount sufficient to establish a circulating dosage of polypeptide of about 10 to about 50 μg, and preferably from about 10 to about 20 μg, in the subject. This corresponds to about 0.2 μg to about 1 μg, and preferably from about 0.2 to about 0.4 μg, of polypeptide per kilogram of body weight. This may be achieved directly by intravenous injection, or it may be achieved indirectly by intranasal administration, i.e., in the form of nose drops. In the latter case, however, the dosage of polypeptide per individual should be about ten times the desired circulating dosage. Thus, an intranasal dosage of polypeptide from about 100 to about 500 μg, and preferably from about 100 to about 200 μg (corresponding to from about 2 to about 10, and preferably from about 2 to about 4 μg/kg) is employed.

The polypeptide is administered in solution in a suitable solvent, preferably water. The solution may contain various additives generally known to the art. A preferred medium is physiological saline solution. The solution is preferably acidic having a pH of from about 3 to about 5, and especially about 4, to stabilize the polypeptide. It is also desirable to include small amounts of bacteriostat, e.g., chlorobutanol, to minimize bacterial contamination in the intranasal preparation.

The concentration of polypeptide in the solution is not narrowly critical, and can range from about 1 μg/ml to 1000 μg/ml or higher, depending upon the intended mode of administration and dosage. In general, solutions intended for intranasal applications will contain higher concentrations of polypeptide than solutions intended to be administered by injection. Thus, solutions for intranasal administration ordinarily will contain from about 100 to about 400 μg polypeptide per milliliter, whereas injectable solutions will contain of the order of about 4 to about 10 μg polypeptide per milliliter.

The increase in Factor VIII levels begins within about 15 minutes after administration of polypeptide, and increased levels persist for at least 4 hours. When the circulating dosage of polypeptide is at least 10 μg, the circulating level of Factor VIII is at least 3 times normal, and may be 10 or more times normal. Thus, polypeptide is administered to the donor at least 15 minutes prior to collection, and preferably no more than 2 hours prior to collection.

The blood of the donor is collected in any conventional manner, and is treated by conventional techniques, for example by freeze-drying, to form a dried Factor VIII preparation. Because of the increased concentration of Factor VIII in the blood, the amount of Factor VIII in the dried preparation recovered from a constant volume of blood is correspondingly increased. Furthermore, since the amount of blood constituents other than Factor VIII (and plasminogen activator) is not affected, the proportion of "impurities" in the Factor VIII is reduced.

The following example is illustrative.

Example 1

Intravenous infusions of 10 μg of 1-deamino-6-carba-8-D-arginine vasopressin (dCDAVP) were given to each of five consenting healthy males volunteers aged 26–40 years. After reclining quietly for 30 minutes, each volunteer was infused through a 15-gauge needle introduced into a vein in one antecubital fossa, and blood samples were taken through a 15-gauge needle introduced into a vein in the other antecubital fossa. A Harvard constant-infusion pump first administered 25 ml of sodium chloride solution (154 mmol/1 saline) for 15 minutes, followed by the dCDAVP in 50 ml saline for a further 15 minutes. Blood was sampled before, during and after infusion. Patency of the sampling needle was maintained by an infusion of saline at 1 ml/min. Pulse rate was recorded throughout.

Plasma samples which were recovered from the blood samples were immediately frozen and stored at −40° C. All samples from a single infusion were then thawed and assayed together, usually on the same day as the infusion, but never more than seven days later.

Factor VIII procoagulant activity (VIII-AHF) was assayed by a modification of the activiated partial thromboplastin time using severe hemophilic plasma as the substrate (Hardisty & MacPherson, Thrombosis et Diathesis Haemorrhagica, 7, 215 (1962), as modified by Veltkamp, M.D. Thesis, University of Leiden, The Netherlands, "Detection of Carrier States in Hereditary Coagulation Disorders," Publ. Schatteur-Verlag, Stuttgart (1967)). The assays were standardized against freeze-dried plasma of known Factor VIII content, either the 4th or 6th British standard (obtained from the National Institute for Biological Standards and Control, Holly Hill, Hampstead, London). Some samples were also assayed by the two-stage technique of Biggs et al, British Journal of Haemotology, 1, 20 (1955) using the same Factor VIII standards.

Factor VIII-related antigen (VIII-AGN was assayed by the Laurell method, Scandinavian Journal of Clinical and Laboratory Investigation, 29, Supplement 124, 21 (1972)) using 0.4% antiserum (Behringwerke A.G., Marburg, Germany in 1% agarose, Indubiose, L-Industrie Biologique, Brancaise, Gennevilliers, France). The buffer used was tris-EDTA-borate pH 8.6 (Aronsonn & Gronwall, Scandinavian Journal of Clinical and Laboratory Investigation, 9, 338 (1957)), diluted five-fold. Results were expressed as a percentage of the antigen level in the same freeze-dried plasma as was used to standardize the bioassay. Crossed immunoelectrophoresis was carried out by a similar modification of the original technique of Laurell.

The mean Factor VIII-AHF (reported as international units) and the mean Factor VIII-AGN (reported as the percent of standard plasma) reponses are summarized in tabular form below, together with data obtained in similar fashion except that saline was substituted for the dCDAVP as a control.

| Time, min. | Factor VIII-AHF[1] | | Factor VIII-AGN[1] | |
|---|---|---|---|---|
| | Saline | dCDAVP | Saline | dCDAVP |
| 0 | 0.98 ± 0.07 | 0.99 + 0.11 | 117 + 19 | 126 + 14 |
| 7½ | 1.03 ± 0.07 | 0.97 ± 0.15 | 119 ± 19 | 129 ± 15 |
| 15[2] | 0.92 ± 0.08 | 1.03 ± 0.08 | 128 ± 20 | 135 ± 21 |
| 30 | 0.95 ± 0.06 | 1.65 ± 0.11 | 125 ± 15 | 150 ± 19 |
| 45 | 0.99 ± 0.09 | 2.08 ± 0.16 | 128 ± 17 | 215 ± 29 |
| 60 | 0.97 ± 0.09 | 1.99 ± 0.16 | 131 ± 18 | 214 ± 20 |

[1]Values are presented as the mean ± the standard error of the mean.
[2]Onset of infusion.

As is evident, the administration of dCDAVP to the volunteers resulted in a substantial increase in Factor VIII blood levels.

What is claimed is:

1. In a method for producing a Factor VIII preparation comprising collecting blood from a donor, separating the plasma therefrom, and recovering a Factor VIII-rich fraction from said plasma, the improvement of administering to said donor, in an amount effective to increase the circulating level of Factor VIII in the blood of said donor, a polypeptide represented by the formula:

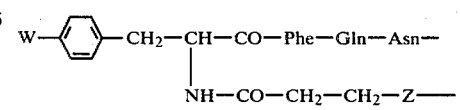

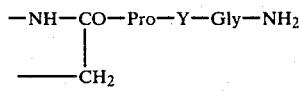

wherein W is hydrogen, hydroxy or amino; Y is a residue of an alpha-amino acid having a basic aliphatic side chain in the D-configuration containing from 2 to 5 carbon atoms and having on the terminal carbon a basic group; and Z is disulfide or monocarba, with the proviso that when W is hydroxy, and Y is the D-arginine residue, then Z is monocarba, and thereafter recovering blood containing said increased levels of Factor VIII.

2. A method according to claim 1 wherein said amount is a circulating drug dosage of at least about 10 micrograms.

3. A method according to claim 2 wherein W is hydroxy, Y is the D-arginine residue and Z is monocarba.

4. A method according to claim 3 wherein said amount is a circulating drug dosage of from about 10 to about 20 micrograms.

5. A method according to claim 2 wherein said administration is intravenously.

6. A method according to claim 2 wherein said administration is intranasally.